US011911525B2

(12) United States Patent
Folwarzny

(10) Patent No.: US 11,911,525 B2
(45) Date of Patent: Feb. 27, 2024

(54) WOUND DRESSING

(71) Applicant: Alexander Folwarzny, Hanau (DE)

(72) Inventor: Alexander Folwarzny, Hanau (DE)

(*) Notice: Subject to any disclaimer, the term of this patent is extended or adjusted under 35 U.S.C. 154(b) by 287 days.

(21) Appl. No.: 16/585,250

(22) Filed: Sep. 27, 2019

(65) Prior Publication Data

US 2020/0101192 A1    Apr. 2, 2020

(30) Foreign Application Priority Data

Sep. 30, 2018  (DE) ............... 10 2018 007 692.0

(51) Int. Cl.
*A61L 15/42*   (2006.01)
*A61F 13/00*   (2006.01)
*A61F 13/02*   (2006.01)
*A61L 31/04*   (2006.01)

(52) U.S. Cl.
CPC ...... *A61L 15/425* (2013.01); *A61F 13/00029* (2013.01); *A61F 13/0209* (2013.01); *A61L 31/04* (2013.01)

(58) Field of Classification Search
CPC ...... A61L 15/425; A61L 31/04; A61L 31/146; A61L 15/00; A61L 26/00; A61F 13/00021; A61F 13/00042; A61F 13/02; A61F 13/0206; A61F 13/00; A61F 13/00008; A61F 13/00029; A61F 13/0209; A61F 2013/00089; A61F 2013/00634; A61F 2013/00246; A61F 2013/00251; A61F 2013/00255; A61F 2013/00259; A61F 2013/00582
USPC ...... 602/41, 46, 47, 52, 54, 58, 59; 424/443, 424/445–448; 604/304, 307
See application file for complete search history.

(56) References Cited

U.S. PATENT DOCUMENTS

| | | | |
|---|---|---|---|
| 3,529,597 | A | 9/1970 | Fuzak |
| 4,271,310 | A | 6/1981 | Watanabe et al. |
| 6,278,036 | B1 | 8/2001 | Anhäuser et al. |
| 10,086,107 | B2 | 10/2018 | Cotton |
| 2001/0001110 | A1* | 5/2001 | Bodenschatz ....... A61F 13/0273 602/41 |

(Continued)

FOREIGN PATENT DOCUMENTS

| | | | | |
|---|---|---|---|---|
| CA | 2665184 | A1 * | 4/2008 | ....... A61F 13/00017 |
| DE | 10 2008 062 472 | A1 | 12/2008 | |

(Continued)

OTHER PUBLICATIONS

German Office Action corresponding to German Application No. 10 2018 007 692.0, dated Jul. 15, 2019.

(Continued)

*Primary Examiner* — Caitlin A Carreiro
(74) *Attorney, Agent, or Firm* — LADAS & PARRY LLP; Malcolm J. MacDonald, Esq.

(57) ABSTRACT

A wound dressing (10) for covering a wound, including an absorbent layer (12) with an upper side (14) and a lower side (18), the upper side being coated with a protective layer (16). At least one cut (26) and at least one perforated dividing line (28) is incorporated into the absorbent layer (12) to form at least one segment (30, 32, 34, 36), which can be separated from the absorbent layer (12) without tools. An adhesive section (40) originates from the protective layer (16) for covering the at least one cut (26) and the at least one perforated dividing line (28).

15 Claims, 8 Drawing Sheets

(56) References Cited

U.S. PATENT DOCUMENTS

Figure 1:
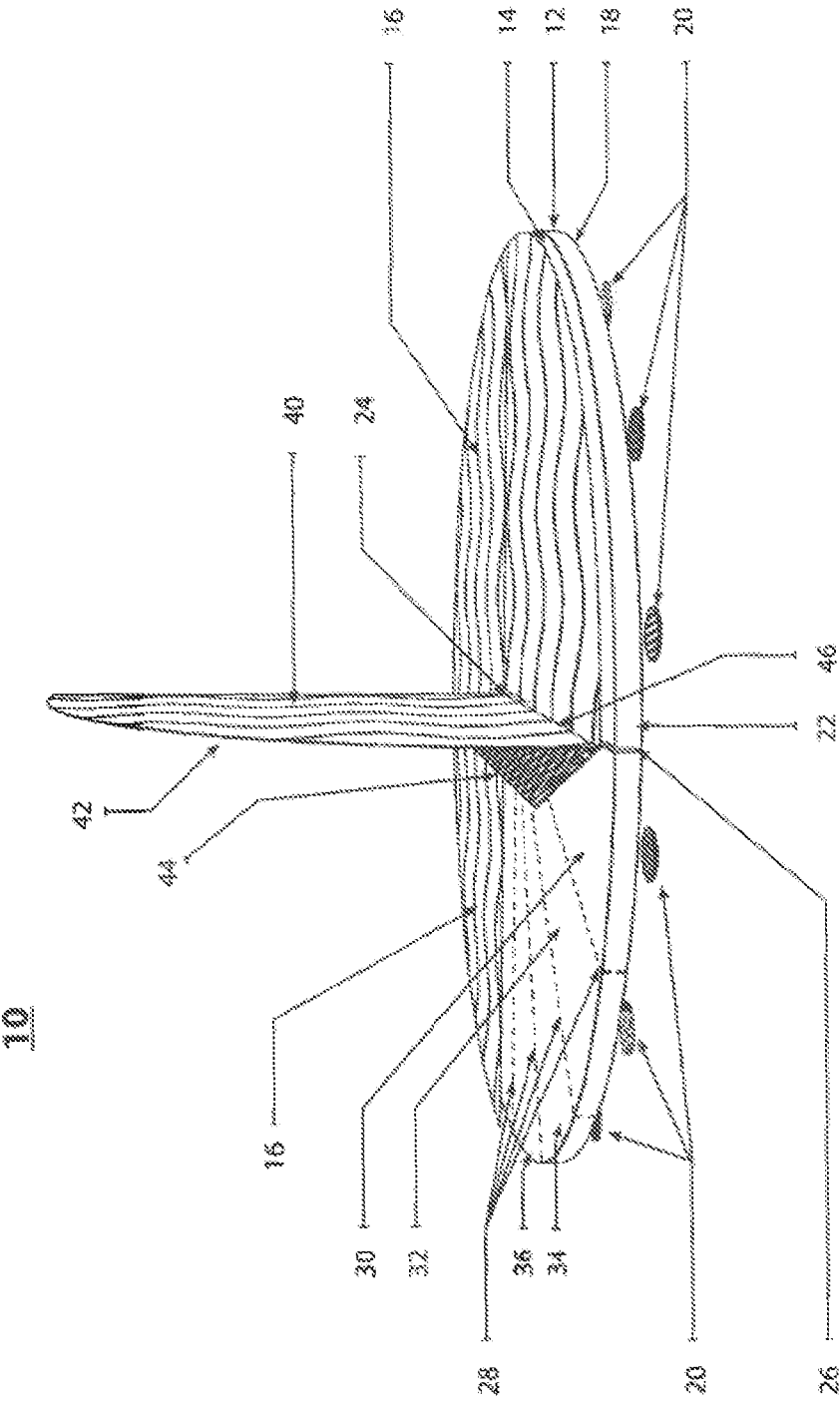

| | | | |
|---|---|---|---|
| 2004/0030304 A1* | 2/2004 | Hunt | A61F 13/00068 |
| | | | 604/317 |
| 2011/0213287 A1* | 9/2011 | Lattimore | A61F 13/00017 |
| | | | 604/319 |
| 2014/0188090 A1 | 7/2014 | Riesinger | |
| 2015/0032069 A1* | 1/2015 | Ko | A61F 13/00029 |
| | | | 604/360 |
| 2015/0182677 A1* | 7/2015 | Collinson | A61F 13/00042 |
| | | | 604/319 |

FOREIGN PATENT DOCUMENTS

| | | | | |
|---|---|---|---|---|
| WO | 97/21459 A1 | 6/1997 | | |
| WO | WO-9721459 A1 * | 6/1997 | | A61M 25/02 |
| WO | 2010092334 A1 | 8/2010 | | |
| WO | 2014140608 A1 | 9/2014 | | |
| WO | WO-2015173546 A1 * | 11/2015 | | A61F 13/00068 |
| WO | WO-2015193257 A1 * | 12/2015 | | A61F 13/00008 |
| WO | WO-2017173132 A1 * | 10/2017 | | A61F 13/4704 |

OTHER PUBLICATIONS

Office Action from European Patent Office, dated Feb. 7, 2020, in corresponding EP Application No. 19200449.

* cited by examiner

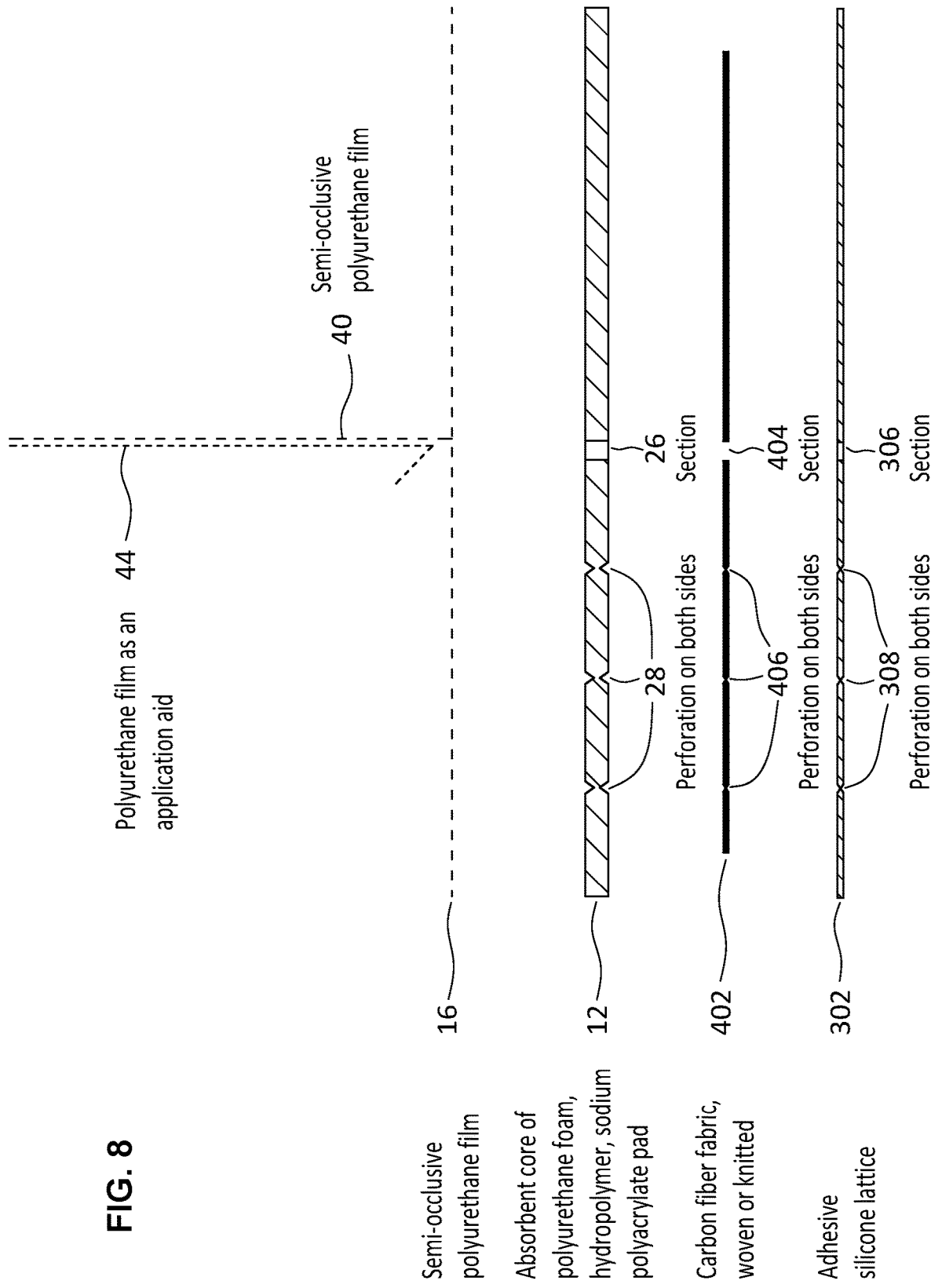

WOUND DRESSING

The invention relates to a wound dressing, comprising an absorbent layer, such as a polyurethane foam layer, with an upper side, which is coated with a protective layer, such as a semi-occlusive polyurethane film, at least in areas, and a lower side, which is preferably coated with an adhesive layer, such as an adhesive silicone layer.

Wound dressings are known from the prior art, particularly foam dressings for the treatment of exudating wounds which are sold, e.g., under the trade name SymbioFoam. The known wound dressings comprise an absorbing layer, preferably in the form of a PU foam layer with an upper side, which is coated with a protective layer, preferably semi-occlusive polyurethane film. A lower side of the absorbent layer may be coated with an adhesive layer of an adhesive silicone layer, such as a silicone lattice or silicone pad.

The wound dressings known from the prior art are formed as a flat, preferably rectangular dressing. To treat wounds on areas of the body having curved surfaces such as the heel, elbow, breast, armpit, or shoulder, the known wound dressings are often not well-suited.

DE 10 2011 050 047 A1 relates to a wound care article for cavities, comprising at least one flat layer, wherein the flat layer is formed in the shape of a propeller, with at least two blades and a central region, wherein the blades are arranged about the central region of the propeller and the blades are connected to one another via the central region. A removal of segments, however, is not provided.

DE 20 2007 019 565 U1 relates to a wound dressing in the form of an adhesive laminate, which forms a removable cover, which has tabs, to enable grasping and pulling off. In doing so, the wound dressing may be perforated and even the dividing liner as well. The perforation provides ventilation without the segments to be separated being required.

WO 97/21459 A1 relates to a device, which comprises a plaster, which can be covered, on the skin side, by a film having a slit. There is no separation of segments of an absorbent layer.

EP 0 026 572 B1 relates to a wound dressing with multiple layers, of which one may be a carbon fiber fabric.

U.S. Pat. No. 3,529,597 B relates to a fingertip bandage, which consists of multiple sections separated by slits. A separation of segments is not described.

DE 296 21 366 U1 relates to an application aid for bandages and is characterized in that a removable protective film is provided, which covers a polymer film and an adhesive film attached thereto before use. The protective layer has wings to facilitate removal.

DE 10 2008 062 472 A1 relates to a wound bandage, which is provided for negative-pressure therapy. In this case, the bandage has a wound contact layer with protrusions and recesses in order to achieve contact with a skin surface in the area of the protrusions.

Starting from here, the object of the present invention is to further develop a wound dressing of the aforementioned type such that an application onto areas of the body with a strongly curved surface contour is enabled in a simple manner.

The object is achieved according to the invention in that at least one cut and/or at least one perforated dividing and/or tear line is incorporated into the absorbent layer to form at least one segment, which can be separated from the absorbent layer without tools, and that the absorbent layer can be sealed in a waterproof and bacteria-proof manner after separation of at least one segment from the layer by means of a detached adhesive section originating from the protective layer, upon the simultaneous coverage of the at least one cut, which has at least one perforated dividing or tear line and/or at least one segment remaining in the layer.

According to the invention, at least one cut and/or at least one perforated dividing and/or tear line is incorporated into the absorbent layer to form at least one segment, which can be separated from the absorbent layer without tools, wherein the absorbent layer can be sealed in a waterproof and bacteria-proof manner after separation of at least one segment from the layer by means of a detached adhesive section originating from the protective layer, upon the simultaneous coverage of the at least one cut, which has at least one perforated dividing or tear line and/or at least one segment remaining in the layer.

In comparison with the prior art, the advantage is achieved that the wound dressing can be adapted individually to areas of the body with a strongly curved surface by means of separating segments from the absorbent layer in a simple manner. Securing and protection from water and bacteria is achieved over the entire surface by means of the detached adhesive section originating from the protective layer.

According to a preferred embodiment, the absorbent layer is formed in a circular shape, wherein the cut in the layer extends, originating from a circumferential edge, in the direction of a center, such as a central point, wherein the perforated dividing and/or tear lines are formed, starting from the circumferential edge, in the direction of the central point, in a circular sector connected to the cut in the circumferential direction, in order to form the separable segments in the form of circular sector segments.

Preferably, the protective layer is formed in a circular shape and is connected, such as bonded, to the upper side of the absorbent layer in the region outside of the separable circular sectors, wherein the detached adhesive section is an integral component of the protective layer and is connected to the protective layer along a bending line extending parallel or substantially parallel to the cut.

A further preferred embodiment is characterized in that the absorbent layer is formed in a circular shape and is coated with the circular-shaped protective layer over the entire surface, wherein the cut as well as the perforated dividing and/or tear lines are formed in both the absorbent layer and the protective layer, wherein the detached adhesive section is formed as a separate adhesive section, comprising a tab, which is connected, such as bonded, on a surface of the protective layer along the cut, wherein the adhesive section extends, in the form of a fin, from the tab along a bending line.

Furthermore, it is proposed that the protective film has two sections, wherein a first section is formed in a semicircular shape and is connected, such as bonded, to the upper side of the absorbent layer over the entire surface, and wherein a second section is formed in a semicircular shape and has a first partial region, which is connected, such as bonded, to the upper side and a second partial region, which is connected to the first partial region via a bending line and forms the detached adhesive section.

In order to obtain a waterproof and bacteria-proof surface, it is provided that the tab with the adhesive section and/or the second section of the protective layer has a radial extension L, which is greater than a radius R of the absorbent layer and/or, that the first and second sections form an overlapping region along a diagonal.

The detached adhesive section preferably has a surface, which is greater than a surface spanned by the circular sector sections.

For simplified application, it is provided that the detached adhesive section has an adhesive surface, which is covered with a cover film.

Especially preferably, it is provided that the absorbent layer is a PU foam layer and/or a hydropolymer or sodium polyacrylate pad, and/or that the protective layer and the detached adhesive layer are semi-occlusive polyurethane film and/or that the adhesive layer is an adhesive silicone lattice or has adhesive silicone pads.

A carbon fiber fabric may preferably be arranged between the lower side of the absorbent layer and the adhesive layer. The cut and/or the perforated dividing and/or tear lines are formed in the absorbent layer, the carbon fiber fabric, as well as the adhesive layer.

Further details, advantages, and features of the invention result not only from the claims, the features to be taken from said claims—on their own and/or in combination—as well as the preferred exemplary embodiments to be obtained from the following description of the drawings.

Figure 2:
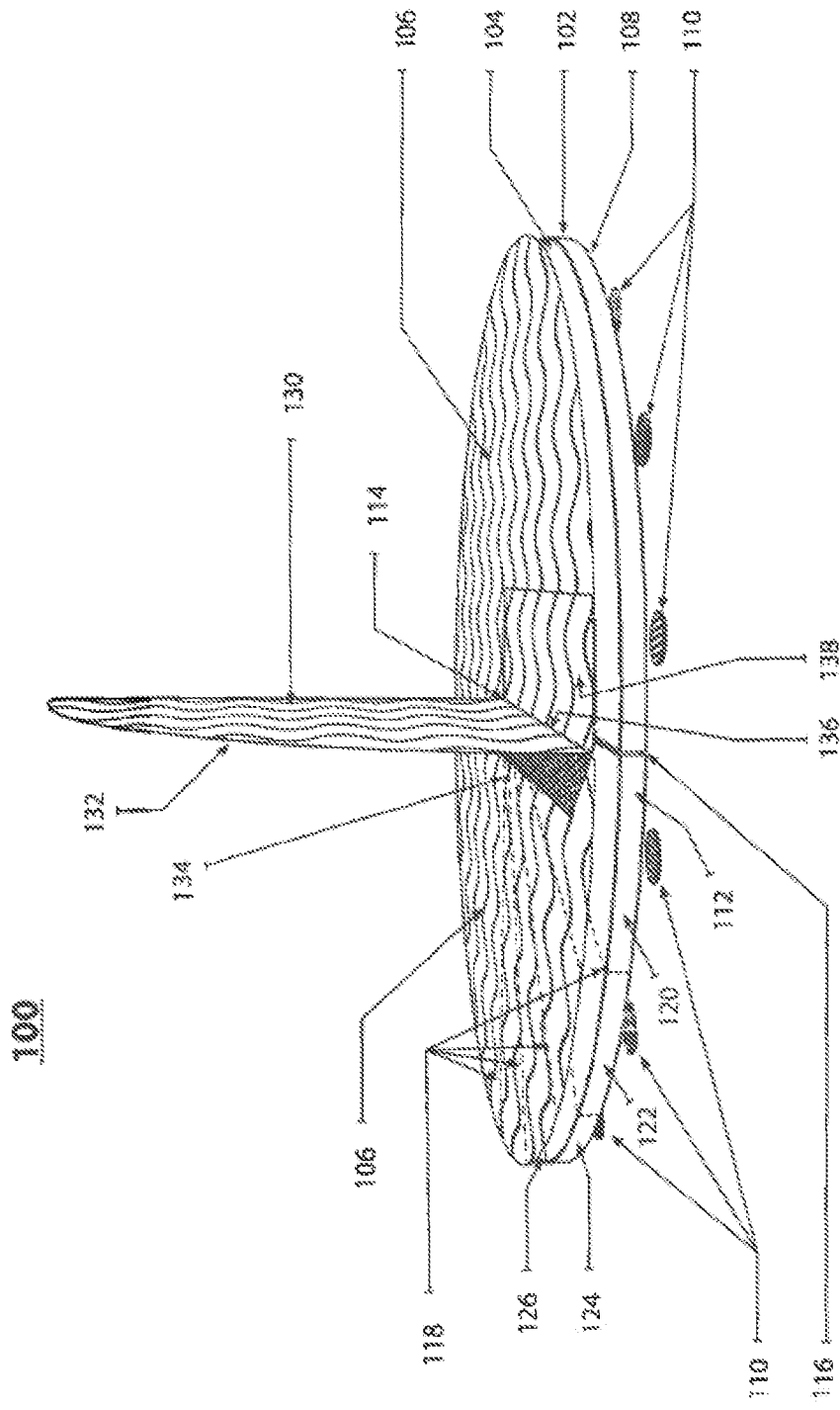
Figure 3:
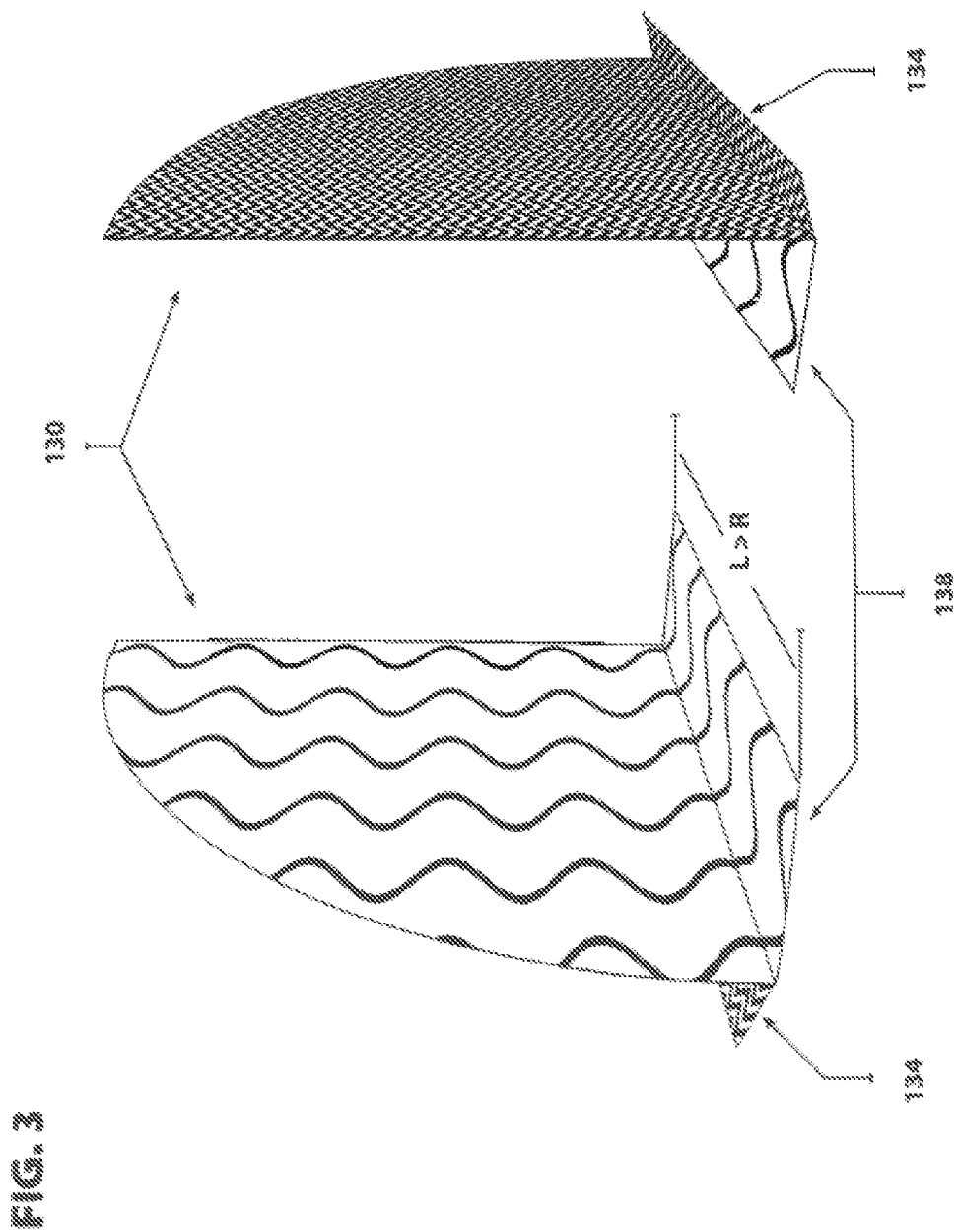
Figure 4:
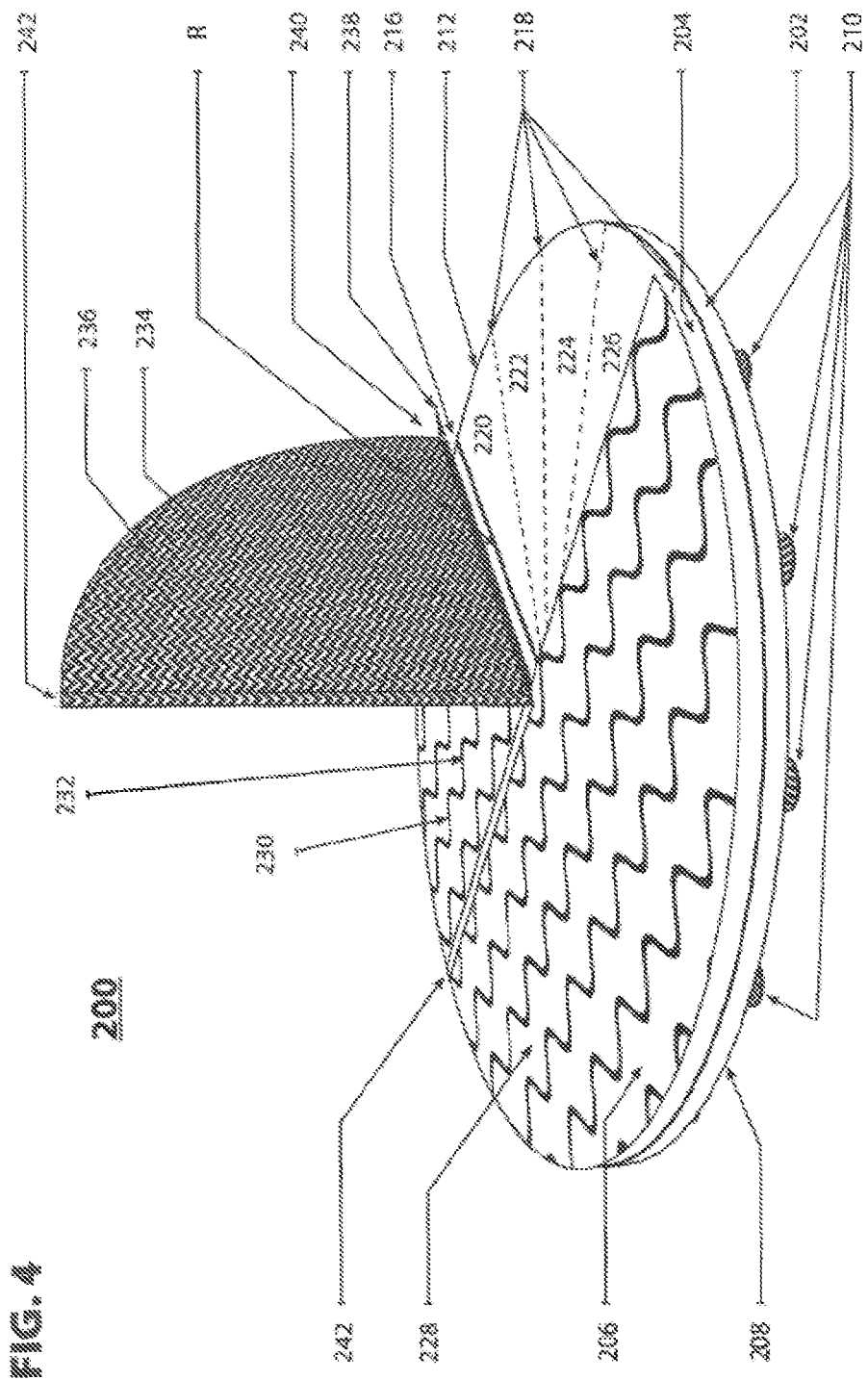
Figure 5:
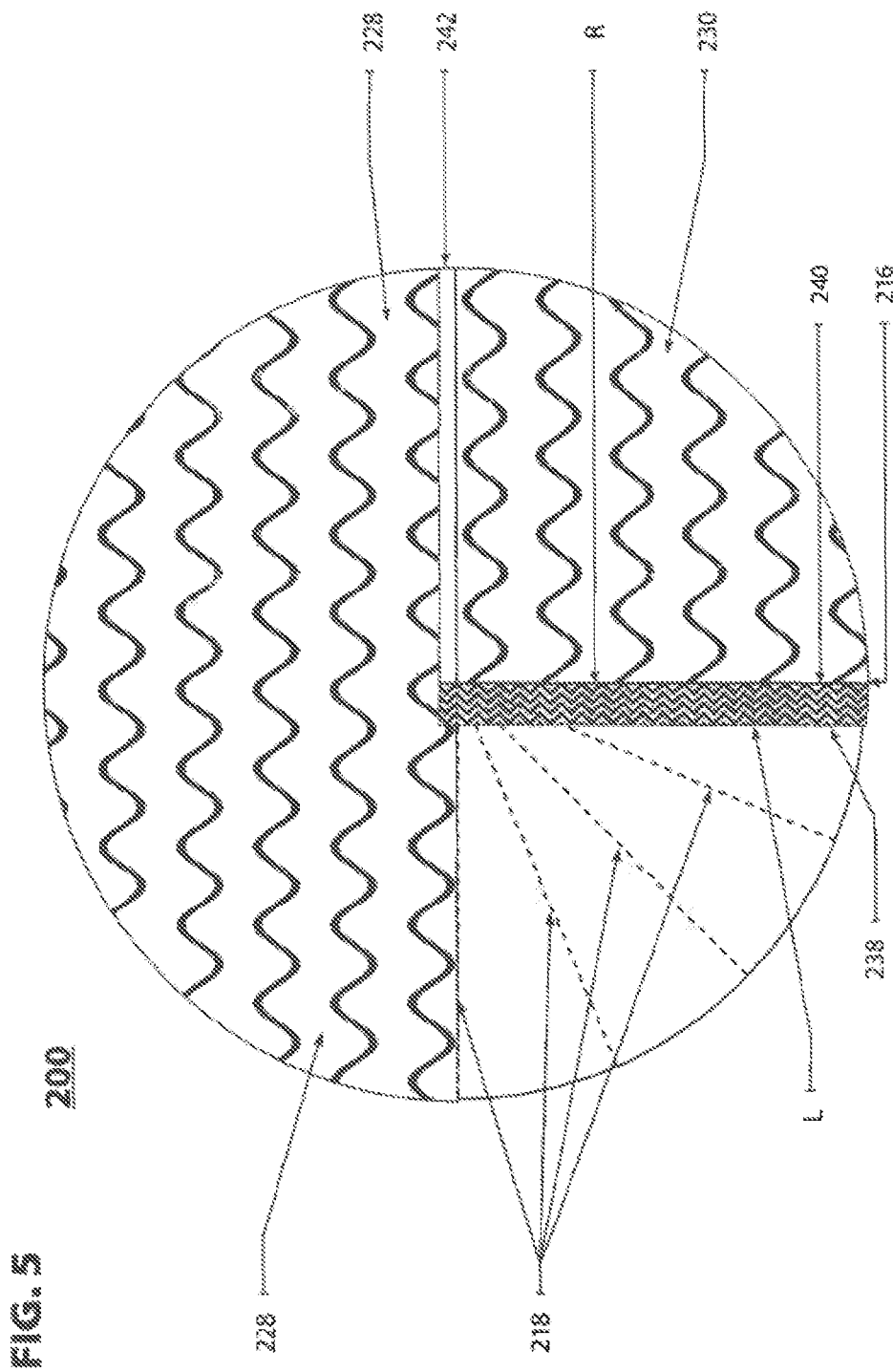
Figure 6:
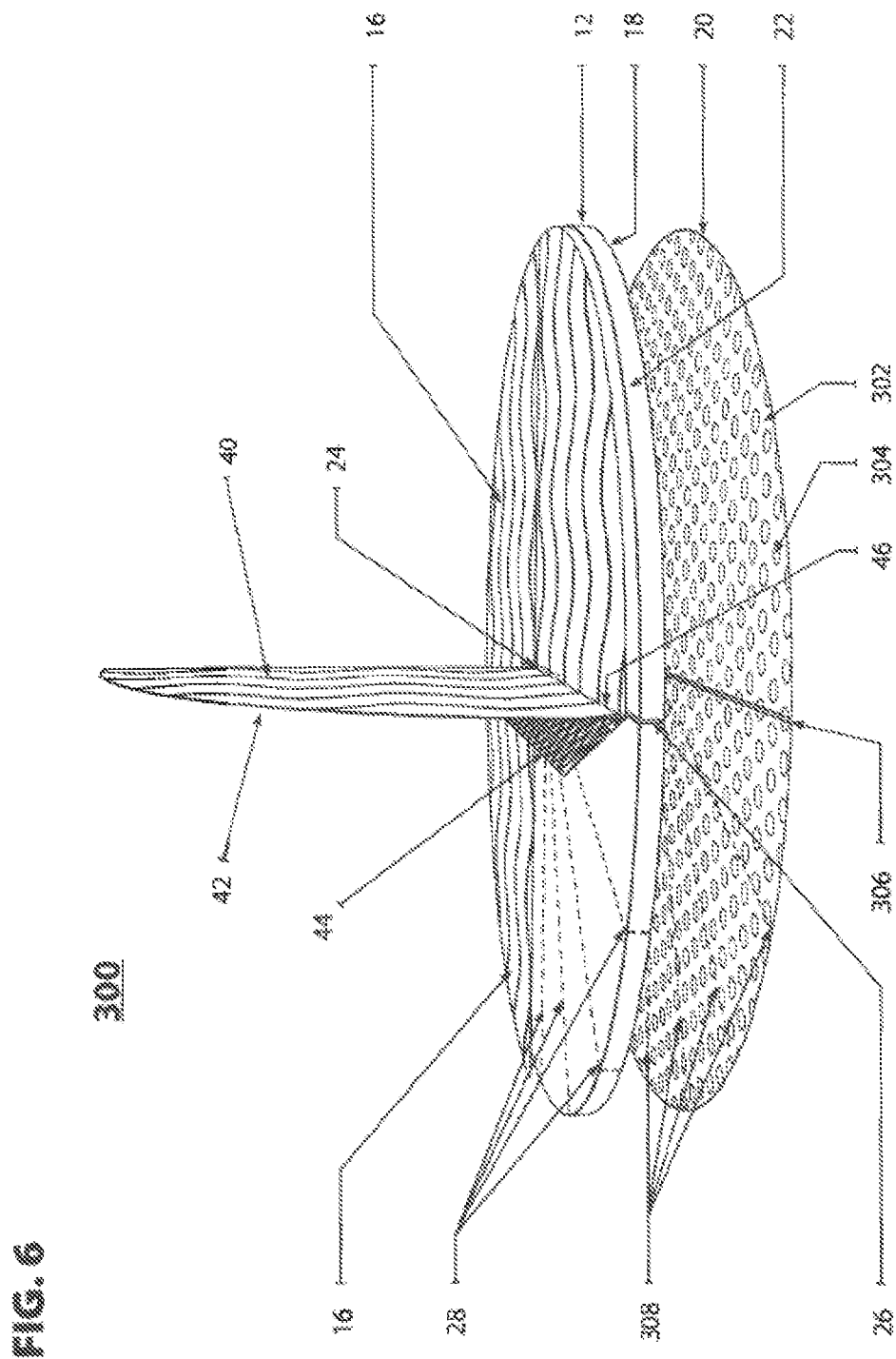
Figure 7:
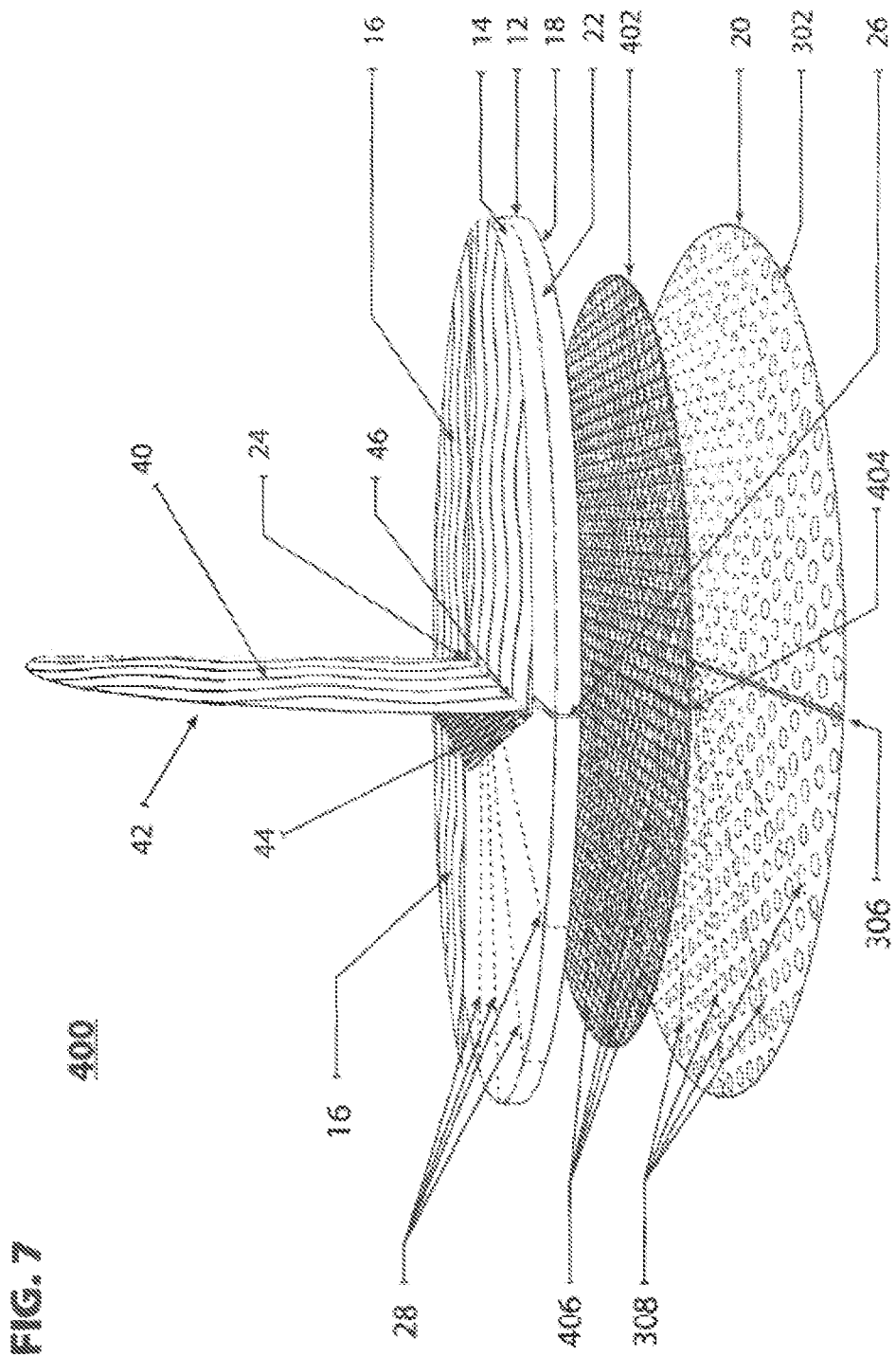

The following is shown:

FIG. 1 a perspective representation of a first embodiment of a foam dressing according to the invention;

FIG. 2 a perspective representation of a second embodiment of a foam dressing according to the invention;

FIG. 3 a detailed view of an application aid of the second embodiment according to FIG. 2;

FIG. 4 a perspective representation of a third embodiment of a foam dressing according to the invention;

FIG. 5 a top view of the third embodiment according to FIG. 4;

FIG. 6 a perspective representation of a fourth embodiment of a foam dressing according to the invention;

FIG. 7 a perspective representation of a fifth embodiment of a foam dressing according to the invention; and FIG. 8 a layer structure of the foam dressing according to FIG. 7.

FIG. 1 shows, in a perspective view, a first embodiment of a wound dressing 10 according to the invention, comprising an absorbent layer in the form of a polyurethane foam layer 12, the upper side 14 of which is coated, at least in areas, with a protective layer, such as waterproof and bacteria-proof, semi-occlusive polyurethane film 16. A lower side 18 of the polyurethane foam layer 12 has an adhesive layer 20 in the form of adhesive silicone pads, at least in sections.

According to the invention, it is provided that the polyurethane foam layer 12 is formed in a circular shape, wherein a cut 26 and/or a preferably perforated dividing and/or tear line 28 is formed in the polyurethane foam layer 12 in the radial direction, starting from an outer edge 22 of the polyurethane foam layer 12 up to a central point 24.

In the exemplary embodiment shown, one or more preferably perforated dividing and/or tear lines 28 are incorporated in the PU foam 12, extending from the outer edge 22 to the central point 24 in a circular sector adjacent to the cut 26 in the circumferential direction. Individual circular sector sections 30-36, which can be removed from the PU foam layer 12 without tools, are formed by the dividing lines 28. After separation of one of the circular sector sections, a truncated-cone-shaped wound dressing adapted to a curved body contour can be formed from the circular, flat wound dressing.

According to the embodiment shown in FIG. 1, the upper side 14 of the PU foam 12 is covered with the semi-occlusive polyurethane film 16 in the area outside of the separable circular sector sections 30-36. In order to cover the circular sector sections 30-36, the PU film 16 has a detached film section 40 in the form of a fin, with an adhesive surface 42 on the back, which is provided with a cover film 44. The film section 40 is an integral component of the PU film 16 and is articulated on the PU film 16 along a bending line 46. The bending line 46 extends parallel or substantially parallel to the cut 26.

With respect to production of the wound dressing 10 according to FIG. 1, it should be noted that, in a first process step, the PU foam layer 12 is produced in the form of a circular area, and subsequently or simultaneously the cut 26 as well as the dividing and/or tear lines 28 are incorporated into the PU foam layer to form these circular sector sections 30-36. The PU film 16 with the film section 40 can then be applied, such as bonded, to the upper side 14 of the PU foam 12. Subsequently or simultaneously, the adhesive layer, which is the adhesive silicone pads 20 in the exemplary embodiment shown, can be applied, such as bonded, to the lower side 18 of the PU foam layer 12.

With respect to use of the wound dressing 10, it should be noted that one or more circular sector sections 30, 32, 34, 36 of the PU foam layer 12 can be separated according to the wound and/or place on the body to be treated. Following this, the flat PU foam layer 12 can be formed into a truncated-cone-shaped surface, wherein a cutting edge of the cut 26 lies on a tear-off edge of a dividing and/or tear line 28. The protective film 44 can then be separated from the adhesive section 40, and the adhesive section 40 can be bonded via the remaining circular sector sections 30-36 such that the upper side 14 of the PU foam layer 12, particularly the dividing and/or tear lines 28, is covered by the PU film 16 without gaps.

FIG. 2 shows a second embodiment of a wound dressing 100, comprising an absorbent layer in the form of a circular PU foam layer 102, the upper side 104 of which is coated, over the entire surface, with a protective layer, such as a semi-occlusive PU film 106.

A lower side 108 is coated in sections with an adhesive layer 110, which has a plurality of silicone pads 110 in the exemplary embodiment shown, which are arranged on the lower side 108 of the PU foam layer 102 in any form.

According to the invention, it is provided with the wound dressing 100 that a cut 116 and/or at least one preferably perforated dividing and/or tear line 118 in the PU foam layer 102 extends in the radial direction, starting from a circumferential edge 112 up to a central point 114 of the PU foam layer 102 as well as the PU film 106. Furthermore, further dividing and/or tear lines 118 are incorporated into the PU foam layer 102 as well as the PU film 116, which likewise extend from the circumferential edge 112 in the direction of the central point 114. Circular sector sections 120, 122, 124, 126, which can be removed from the PU foam layer 102 without tools, are thereby formed.

The wound dressing 100 shown in FIG. 2 differs from the wound dressing 10 shown in FIG. 1 in that the semi-occlusive PU film 106 is bonded onto the upper side 104 of the PU foam layer 102 over the entire surface and consequently also contains the perforated dividing and/or tear lines 118 and/or the cut 116. With this embodiment as well, the circular sectors 120, 122, 124, 126 can be separated without tools in a simple manner in order to adapt the wound dressing 100 to a curved body contour.

In order to cover the perforated dividing and/or tear lines 118, it is provided with the wound dressing 100 according to the invention that a separate detached film section 130, in the form of a fin, is arranged along the cut 116. The film section 130 from a semi-occlusive PU film has an adhesive surface 132 on the back, said adhesive surface being protected by a separable cover film 134. The film section 130 is connected to a tab 138 via a bending line 136, wherein the bending line 136 extends parallel or substantially parallel to the cut 116. The tab 138 has an adhesive surface on the lower side and is bonded with the upper side of the PU film 106.

The wound dressing 100 is particularly characterized in that the area of the film section 130 is greater than the area of the circular sector in which the perforated dividing and/or tear lines 118 are formed. Consequently, the wound dressing 100 can also be used in a flat, even state, i.e. when no circular sector sections are torn out, without limitation with respect to the waterproof and bacteria-proof characteristic. The film section 130 of the PU film 106 ensures that the surface of the PU foam layer 102 is covered completely.

FIG. 3 shows a front and back view of the film section 130 in a perspective representation. The adhesive tab 138 is preferably formed in a rectangular shape and has a length L, which is greater than a radius R of the wound dressing. This ensures an overlapping region between the PU film 106 and the film section 130 with a flat, even application of the wound dressing 100. Alternatively, it may be provided that the film section 130 has a circumferential extension, which is greater than the circumferential extension of the circular sector sections 120, 122, 124, 126.

FIG. 4 shows, in a perspective representation, a third embodiment of a wound dressing 200. The wound dressing 200 comprises an absorbent layer 202 from a circular PU foam layer with an upper side 204, on which a semi-occlusive polyurethane film 206 is applied, such as bonded. An adhesive layer 210, in the form of adhesive silicone pads, is applied to a lower side 208, at least in areas.

According to the invention, a cut 216 is incorporated into the PU foam layer 202 starting from a circumferential edge 212 up to the central point 214. Furthermore, one or more preferably perforated dividing lines 218 are provided in the circumferential direction, which extend from the circumferential edge 212 in the direction of the central point 214 and subdivide a circular sector of the PU foam layer 202 into circular sector sections 220-226, which can be separated without tools. The separable circular sector sections 220-226 are not covered by a semi-occlusive polyurethane film.

According to the design of the wound dressing 200 according to the invention, it is provided that the semi-occlusive polyurethane film 206 has two sections, namely a first section 228, which is preferably formed in a semicircular shape and covers a first half of the circular PU foam layer 202. Furthermore, a second section 230 is provided, which is likewise formed in a semicircular shape, wherein a first sub-section 232 of the second section 230 is bonded to the upper side 204, and a second sub-section 234 forms a detached film section, in the form of a fin, with an adhesive surface 236 and cover film 238, and is connected to the first sub-section 232 via a bending line 240.

FIG. 5 shows a top view of the wound dressing 200. The second section 230 of the semi-occlusive polyurethane film has a length L, which is greater than a radius R of the PU foam layer, such that an overlapping region 242 results in the area of a joint between the first semicircular section 228 and the first sub-section 232 as well as the second sub-section 234, in order to achieve complete coverage of the upper side of the PU foam layer 202.

During the application of the wound dressing 200 onto a wound, a circular sector section 220-226 can be separated from the PU foam layer 202 without tools, just as with the previously described embodiments, and the wound dressing 200 can then be placed into the corresponding shape. Subsequently, the cover film 238 can be separated and the second sub-section 234, in the form of the fin, can be bonded to the remaining circular sector sections in order to form a closed surface.

The wound dressing 200 is also characterized in that it can be used in flat form, i.e. without separation of the circular sector sections 220-226, and a sufficient seal against water and bacteria is still assured.

FIG. 6 shows a fourth embodiment of a wound dressing 300, which substantially corresponds to the embodiment of wound dressing 10, wherein the adhesive layer 20 is formed in the form of an adhesive silicone lattice 302, which is formed in a circular shape in accordance with the shape of the PU foam layer and is connected, such as bonded, to the lower side 18 of the PU foam layer 12. Perforations, such as holes 304, are formed in the adhesive silicone lattice 302, whereby wound contact is established with the PU foam 12. Furthermore, a cut 306 as well as correspondingly perforated dividing and/or tear lines 308 are incorporated into the silicone lattice in the radial direction. Preferably, the adhesive silicone lattice 302 is already connected to the PU foam 12, wherein subsequently the cut 26 and/or 306 as well as the dividing and/or tear lines 28, 308 are incorporated in a common process step.

The application of wound dressing 300 takes place in accordance with the application of wound dressing 10 according to FIG. 1.

FIG. 7 shows, in a perspective representation, a fifth embodiment of a wound dressing 400. Wound dressing 400 substantially corresponds to wound dressing 300 according to FIG. 6, wherein a carbon fiber fabric 402, in woven or knitted form, is arranged between the adhesive layer 20 and the lower side 18 of the PU foam layer 12. In terms of the invention, a cut 404 and/or perforated dividing and/or tear lines 406 are incorporated in the carbon fiber fabric 402, also in the radial direction.

During production of the wound dressing 400, first the PU foam layer 12, the carbon fiber fabric 402, as well as the adhesive silicone lattice 302 are connected to each other like a sandwich and subsequently the cut 26, 306, 404 and/or the perforated separating and/or tear lines 28, 308, 406 are incorporated. The semi-occlusive polyurethane film 16 with film section 40 can then be bonded to the upper side 14 of the PU foam 12.

FIG. 8 shows, purely schematically, a layer structure of the wound dressing 400 in an exploded view.

The invention claimed is:

1. A wound dressing for a curved body contour, comprising:
    a circular absorbent layer having a center, a circumferential edge, an upper side, and a lower side;
    a protective layer disposed on the upper side;
    an adhesive layer disposed on the lower side; and
    at least one perforated tear line in the absorbent layer that extends radially from the center to the circumferential edge of the absorbent layer;
    wherein at least one sector of the absorbent layer is limited by, and is separable along, either:
    the at least one perforated tear line and a first cut in the absorbent layer that extends radially from the center to the circumferential edge of the absorbent layer; or
    the first cut and a second cut in the absorbent layer that extends radially from the center to the circumferential edge of the absorbent layer;
    wherein the absorbent layer is sealable in a waterproof and bacteria-proof manner after separation of the at least one sector from the absorbent layer by means of a detached adhesive section originating from the protective layer, upon the simultaneous coverage of the at least one perforated tear line and the first cut, or the first cut and the second cut; and wherein the absorbent layer is formable into a truncated cone shape configured to fit a curved body contour after separation of the at least one sector.

2. The wound dressing according to claim 1, wherein the protective layer comprises:
a first section formed in a semicircular shape, and is connected to the upper side of the absorbent layer over the entire upper side, and
a second section formed in a semicircular shape, and has a first partial region connected to the upper side, and a second partial region connected to the first partial region via a bending line, and forming the detached adhesive section.

3. The wound dressing according to claim 2, wherein the tab with the detached adhesive section, and/or the second section of the protective layer has a radial extension greater than a radius of the absorbent layer, and/or that the first and second sections form an overlapping region along a diagonal.

4. The wound dressing according to claim 1, wherein the protective layer is formed in a circular shape, and is connected to the upper side of the absorbent layer in a region outside the at least one sector, and wherein the detached adhesive section is an integral component of the protective layer, and is connected to the protective layer along a bending line extending parallel, or substantially parallel, to the first cut.

5. The wound dressing according to claim 1, wherein the absorbent layer is coated with the protective layer over the entire upper side,
wherein the first cut and the at least one perforated tear line are formed in the absorbent layer and the protective layer,
wherein the detached adhesive section is formed as a separate adhesive section, comprising a tab connected to a surface of the protective layer along the first cut, and
wherein the detached adhesive section extends, in the form of a fin, from the tab along a bending line.

6. The wound dressing according to claim 1, wherein the detached adhesive section has an area that is greater than an area spanned by circular sector sections.

7. The wound dressing according to claim 1, wherein the detached adhesive section has an adhesive surface covered with a film.

8. The wound dressing according to claim 1, wherein the absorbent layer is a polyurethane foam layer, and/or that the protective layer and the detached adhesive layer are semi-occlusive polyurethane film, and/or that the adhesive layer is an adhesive silicone lattice, or has adhesive silicone pads.

9. The wound dressing according to claim 1, wherein a carbon fiber fabric is arranged between a lower side of the absorbent layer and the adhesive layer, and/or that the first cut and the at least one perforated tear line are formed in the absorbent layer, the carbon fiber fabric, and the adhesive layer.

10. The wound dressing according to claim 1, wherein the lower side of the absorbent layer is coated with an adhesive silicone layer.

11. The wound dressing according to claim 1, wherein the absorbent layer is a polyurethane foam layer.

12. The wound dressing according to claim 1, wherein the protective layer is a semi-occlusive polyurethane film.

13. The wound dressing according to claim 1, wherein the wound dressing has a flat truncated cone shape after separation of the at least one sector.

14. The wound dressing according to claim 1, wherein the at least one sector of the absorbent layer is limited by, and is detachable along, the at least one perforated tear line and a first cut in the absorbent layer that extends radially from the center to the circumferential edge of the absorbent layer; and wherein the absorbent layer is sealable in a waterproof and bacteria-proof manner after separation of the at least one sector from the absorbent layer by means of a detached adhesive section originating from the protective layer, upon the simultaneous coverage of the at least one perforated tear line and the first cut.

15. The wound dressing according to claim 1, wherein the at least one sector of the absorbent layer is limited by, and is detachable along, the first cut and a second cut in the absorbent layer that extends radially from the center to the circumferential edge of the absorbent layer; and wherein the absorbent layer is sealable in a waterproof and bacteria-proof manner after separation of the at least one sector from the absorbent layer by means of a detached adhesive section originating from the protective layer, upon the simultaneous coverage of the first cut and the second cut.

* * * * *